(12) United States Patent
Tanaka et al.

(10) Patent No.: US 7,776,619 B2
(45) Date of Patent: Aug. 17, 2010

(54) METHOD OF STABILIZING PULMONARY SURFACTANT PROTEIN

(75) Inventors: Seiji Tanaka, Choshi (JP); Masaru Hamaoki, Choshi (JP)

(73) Assignee: Yamasa Corporation, Choshi-shi (JP)

( * ) Notice: Subject to any disclaimer, the term of this patent is extended or adjusted under 35 U.S.C. 154(b) by 205 days.

(21) Appl. No.: 11/913,797

(22) PCT Filed: May 10, 2006

(86) PCT No.: PCT/JP2006/309374

§ 371 (c)(1),
(2), (4) Date: Nov. 7, 2007

(87) PCT Pub. No.: WO2006/121064

PCT Pub. Date: Nov. 16, 2006

(65) Prior Publication Data

US 2009/0239309 A1 Sep. 24, 2009

(30) Foreign Application Priority Data

May 11, 2005 (JP) ............................. 2005-138113

(51) Int. Cl.
*G01N 33/53* (2006.01)
(52) U.S. Cl. ..................................................... 436/518
(58) Field of Classification Search ........................ None
See application file for complete search history.

(56) References Cited

U.S. PATENT DOCUMENTS 6,172,203 B1    1/2001  Hager et al.
2003/0212248 A1 * 11/2003  Furman ...................... 530/303

FOREIGN PATENT DOCUMENTS

| JP | 3 44332 | 2/1991 |
| JP | 2001-33450 | 2/2001 |
| JP | 3573330 | 7/2004 |
| WO | WO 91/00871 | 1/1991 |

OTHER PUBLICATIONS

Bi, Xiaohong et al., "Thermal Stability and DPPC/CA$^{2+}$ Interactions of Pulmonary Surfactant SP-A From Bulk-Phase and Monolayer IR Spectroscopy", Biochemistry, vol. 40, pp. 13659 to 13669, 2001.

Mark, L., et al., "Surfactant Function and Composition After Free Radical Exposure Generated by Transition Metals", The American Physiological Society, vol. 276 (3 Pt 1), pp. L491-500, 1999.

Alcorn, John F., et al., "Degradation of Pulmonary Surfactant Protein D by Pseudomonas Aeruginosa Elastase Abrogates Innate Immune Function", The Journal of Biological Chemistry, vol. 279, No. 29, pp. 30871 to 30879, 2004.

Hisato Nagae, et al., "Establishment of the Enzyme-Linked Immunosorbent Assay for Pulmonary Surfactant Protein D in Sera", Igaku to Yakugaku (Japanese Journal of Medicine and Pharmaceutical Science), 36(4), Oct. 1996, pp. 803-808 (with partial English translation).

Rompp, "Zinnchloride", RÖMPP online, XP002539069, Retrieved from the Internet: URL:http://www.roempp.com>, Mar. 2002, 2 pages.

Shuichi Kamada, et al., "A sandwich enzyme immunoassay for pulmonary surfactant protein D measurement of its blood levels in drowning victims", Forensic Science International, vol. 109, No. 1, Mar. 2000, pp. 51-63, 1998.

Database RÖMPP, "Blutplasma", Online, Version 3.6, Jun. 1, 2003, 2 pages.

* cited by examiner

*Primary Examiner*—Jacob Cheu
(74) *Attorney, Agent, or Firm*—Oblon, Spivak, McClelland, Maier & Neustadt, L.L.P.

(57) ABSTRACT

The present invention relates to a method for long-term stabilizing a pulmonary surfactant protein, to a stabilized aqueous solution containing a pulmonary surfactant protein, and to a kit for assaying a pulmonary surfactant protein which kit contains, as a component reagent, a stabilized aqueous solution containing a pulmonary surfactant protein.

The invention provides a method for stabilizing a pulmonary surfactant protein, the method including causing the pulmonary surfactant protein to be present with a calcium ion and an oxidizing/reducing substance.

The invention also provides an aqueous solution containing a pulmonary surfactant protein which has been stabilized by use of a calcium ion and an oxidizing/reducing substance in combination.

The invention also provides a kit for assaying a pulmonary surfactant protein present in a sample through an immunological technique employing antigen-antibody reaction, the kit containing, as a standard solution of pulmonary surfactant protein, an aqueous solution containing a pulmonary surfactant protein which has been stabilized by use of a calcium ion and an oxidizing/reducing substance in combination.

12 Claims, No Drawings

METHOD OF STABILIZING PULMONARY SURFACTANT PROTEIN

TECHNICAL FIELD

The present invention relates to a method for stabilizing a pulmonary surfactant protein, to a stabilized aqueous solution containing a pulmonary surfactant protein, and to a kit for assaying a pulmonary surfactant protein which kit contains, as a component reagent, a stabilized aqueous solution containing a pulmonary surfactant protein.

BACKGROUND ART

Pulmonary surfactant protein is an apo-protein specific to pulmonary surfactant (SP). Hitherto, there have been reported four kinds of pulmonary surfactant protein; i.e., hydrophilic SP-A and SP-D and hydrophobic SP-B and SP-C. Among four kinds of protein, SP-D is considered to play an important role in the defense mechanism in the respiratory tract-alveolus system. It has been reported that pulmonary diseases such as idiopathic interstitial pneumonia can be diagnosed by assaying SP-D of a sample (e.g., serum) through an immunological technique employing antigen-antibody reaction (Non-Patent Document 1).

The above-reported method employs recombinant SP-D (rSP-D) produced through recombinant DNA technology as a standard substance. Although the rSP-D has poor stability, it has also been reported that the stability of pulmonary surfactant proteins including rSP-D can be enhanced through causing an ion of a metal belonging to the sub-group 2-a of a periodic table such as calcium, barium, or magnesium to coexist. (Patent Document 1).

Non-Patent Document 1: Igaku & Yakugaku, 36(4), 803-808 (1996)

Patent Document 1: Japanese Patent No. 3573330

DISCLOSURE OF THE INVENTION

Problems to be Solved by the Invention

Although antigenic activity of pulmonary surfactant protein can be stabilized in the co-presence of an calcium ion, long-term stability of the protein is still to be improved. Specifically, as described in Examples 1 to 3 given in Patent Document 1, the effect of a calcium ion is excellent on stability of pulmonary surfactant protein for a relatively short period of about 6 hours, but the effect of a sole calcium ion is not satisfactory on stability of pulmonary surfactant protein for a middle to long term of 10 hours or longer to several days. In addition, there is keen demand for stability of pulmonary surfactant protein under higher temperature conditions.

Means for Solving the Problems

In order to solve the aforementioned problems, through random screening, the present inventors have found that, merely through exposing pulmonary surfactant protein to the co-presence of a calcium ion and an oxidizing/reducing substance (i.e., substance involved in redox) in combination, antigenic activity is not inactivated but stabilized for 48 hours or longer at 37° C. The present invention has been accomplished on the basis of this finding. Accordingly, the present invention is directed to the following.

[1] A method for stabilizing a pulmonary surfactant protein, the method comprising causing the pulmonary surfactant protein to be present with a calcium ion and an oxidizing/reducing substance.

[2] A method as described in [1] above, wherein antigenic activity of the pulmonary surfactant protein has been stabilized.

[3] A method as described in [1] above, wherein the pulmonary surfactant protein is a recombinant pulmonary surfactant protein D (rSP-D).

[4] A method as described in [1] above, wherein the oxidizing/reducing substance is one or more members selected from among hydrogen peroxide, divalent iron, trivalent iron, divalent manganese, and monovalent copper.

[5] An aqueous solution containing a pulmonary surfactant protein which has been stabilized by use of a calcium ion and an oxidizing/reducing substance in combination.

[6] An aqueous solution as described in [5] above, wherein antigenic activity of the pulmonary surfactant protein has been stabilized.

[7] An aqueous solution as described in [5] above, wherein the pulmonary surfactant protein is a recombinant pulmonary surfactant protein D (rSP-D).

[8] An aqueous solution as described in [5] above, wherein the oxidizing/reducing substance is one or more members selected from among hydrogen peroxide, divalent iron, trivalent iron, divalent manganese, and monovalent copper.

[9] A kit for assaying a pulmonary surfactant protein present in a sample through an immunological technique employing antigen-antibody reaction, the kit containing, as a pulmonary surfactant protein standard solution, an aqueous solution containing a pulmonary surfactant protein which has been stabilized by use of a calcium ion and an oxidizing/reducing substance in combination.

[10] A kit as described in [9] above, wherein antigenic activity of the pulmonary surfactant protein has been stabilized.

[11] A kit as described in [9] above, wherein the pulmonary surfactant protein is a recombinant pulmonary surfactant protein D (rSP-D).

[12] A kit as described in [9] above, wherein the oxidizing/reducing substance is one or more members selected from among hydrogen peroxide, divalent iron, trivalent iron, divalent manganese, and monovalent copper.

Effects of the Invention

According to the present invention, in stabilization of a pulmonary surfactant protein (e.g., rSP-D), the protein is caused to be present with a calcium ion and an oxidizing/reducing substance, specifically, hydrogen peroxide, divalent iron, trivalent iron, divalent manganese, and/or monovalent copper. By virtue of the co-presence, as mentioned in the Examples hereinbelow, antigenic activity of pulmonary surfactant protein can be more stabilized as compared with the sole presence of a calcium ion.

Therefore, according to the present invention, pulmonary surfactant protein can be stored and distributed for a short period and, moreover, for a relatively long term at ambient temperature (25° C.) without inactivation. In addition, reaction in assaying can be performed at ambient temperature to 37° C. Thus, operability and applicability of immunological assay of pulmonary surfactant protein can be further enhanced.

BEST MODES FOR CARRYING OUT THE INVENTION

In the present invention, the term "pulmonary surfactant protein" includes SP-A, SP-B, SP-C, and SP-D. Among them, stabilization is performed preferably for SP-A or SP-D, which has been identified as a useful diagnosis element. Also in the present invention, pulmonary surfactant protein may be a native protein taken from biological tissue and purified, or a recombinant protein produced through recombinant DNA technology.

According to the present invention, pulmonary surfactant protein can be stabilized through co-presence of the protein with a calcium ion and an oxidizing/reducing substance in combination.

The oxidizing/reducing substance which is brought to be present with the protein may be an oxidizing substance or a reducing substance. Examples include one or more members selected from among hydrogen peroxide, divalent or trivalent iron, divalent manganese, and monovalent copper. Among them, hydrogen peroxide and a divalent manganese ion are particularly preferred.

No particular limitation is imposed on the oxidizing/reducing substance concentration. In the case of a substance form such as hydrogen peroxide, the concentration in an aqueous solution containing a pulmonary surfactant protein is preferably 0.001 to 5% (w/v), more preferably 0.01 to 1% (w/v). In the case of metallic ions such as divalent or trivalent iron, divalent manganese, and monovalent copper, the (total) concentration is preferably 0.001 to 1,000 mM, more preferably 0.01 to 100 mM. The concentration of calcium ion to be used in combination in an aqueous solution containing a pulmonary surfactant protein is preferably 0.001 to 100 mM, more preferably 0.01 to 100 mM.

When the oxidizing/reducing substance is in the form of metallic ion, water-soluble metallic salts such as chlorides, acetates, and nitrates are preferably used as a source. Similarly, a water-soluble calcium salt such as calcium chloride, calcium acetate, or calcium nitrate is preferably used as a source of calcium ion.

The aqueous solution containing a pulmonary surfactant protein which has been stabilized by a calcium ion and an oxidizing/reducing substance in combination may be prepared through the following procedure. Specifically, a calcium salt (e.g., calcium chloride) and an oxidizing/reducing substance (hydrogen peroxide, manganese salt, or iron or copper salt (e.g., manganese chloride, iron chloride)) is dissolved in water or a buffer such as HEPES so as to attain the aforementioned concentrations, and a pulmonary surfactant protein in a predetermined amount (e.g., 1 to 200 ng/mL) was dissolved in the solution. Needless to say, no particular limitation is imposed on the chronological order of dissolution, and a pulmonary surfactant protein may be dissolved in advance or simultaneously with the calcium ion and oxidizing/reducing substance.

The thus-prepared stabilized aqueous solution containing a pulmonary surfactant protein is useful as a standard solution of pulmonary surfactant protein for use in a kit for assaying a pulmonary surfactant protein in a sample through an immunological technique employing antigen-antibody reaction. The kit contains an anti-pulmonary surfactant protein antibody as an essential reagent and an optional component such as a labeled anti-pulmonary surfactant protein antibody or a labeled secondary antibody. In addition, the kit contains appropriate reagents required to the selected assay method, for example, turbidimetric immunoassay (TIA), nephelometric immunoassay (NIA), enzyme immunoassay (EIA), fluoro immunoassay (FIA), latex photometric immunoassay (LPIA), chemiluminescent immunoassay (CLIA), electrochemiluminescent immunoassay (ECLIA), or radio immunoassay (RIA). Such kits will next be described in detail, taking an SP-D assay kit for ELISA as an example. The following is an example.

(Kit According to the Present Invention)
  Immobilized anti-SP-D antibody reagent
  Enzyme-labeled anti-SP-D antibody reagent
  SP-D standard antigen solution (containing a calcium ion and a manganese ion)

The above kit for diagnosis may further include generally attached components such as enzymatic reaction substrate liquid, enzymatic reaction-terminating liquid, or washing liquid. Such a kit may be employed in accordance with a known measuring method disclosed in, for example, Igaku & Yakugaku, 36(4), 804-808 (1996).

EXAMPLES

The present invention will next be described in detail by way of examples, which should not be construed as limiting the invention thereto.

Example 1

Stabilization at 37° C.

To a buffer (10 mM HEPES, 150 mM sodium chloride, 10 mM calcium chloride, 1.0% (w/v) bovine serum albumin, and 0.5% (w/v) Triton X-100; pH 7.4), hydrogen peroxide, manganese chloride, iron(II) chloride, iron(III) chloride, or cuprous chloride was added, so that the final concentration of each additive was adjusted to 0.1% (w/v), 10 mM, 5 mM, 1 mM, or 1 mM. The thus-prepared buffers were employed as diluting buffers.

Subsequently, a predetermined amount of rSP-D was added to each diluting buffer, and incubated at 37° C. for 24 to 48 hours. The liquid served as a sample liquid. As a control, the same buffer but containing no hydrogen peroxide, manganese chloride, iron(II) chloride, iron(III) chloride, or cuprous chloride was subjected to the same treatment.

After incubation for 24 hours and 48 hours, SP-D assay of the sample liquid and the control was performed by means of an SP-D assay kit (product of YAMASA Corporation) in accordance with a measuring method disclosed in Igaku & Yakugaku, 36(4), 804-808 (1996) (hereinafter referred to as standard operation method) Table 1 shows the results. As is clear from Table 1, use of a calcium ion and an oxidizing/reducing substance, particularly an iron ion or a manganese ion, in combination, effectively stabilizes antigenic activity of SP-D.

TABLE 1

| Percent activity (%) at Hours 24 and 48 (100% at Hour 0) | | |
| --- | --- | --- |
| Additives | Hour 24 | Hour 48 |
| Control (no additive) | 61 | 44 |
| Manganese chloride | 98 | 91 |
| Iron(II) chloride | 96 | 94 |
| Iron(III) chloride | 96 | 96 |

TABLE 1-continued

Percent activity (%) at Hours 24 and 48 (100% at Hour 0)

| Additives | Hour 24 | Hour 48 |
|---|---|---|
| Cuprous chloride | 80 | 71 |
| Hydrogen peroxide | 83 | 79 |

Example 2

Stabilization at 25° C.

To a buffer (10 mM HEPES, 150 mM sodium chloride, 10 mM calcium chloride, 1.0% (w/v) bovine serum albumin, and 0.5% (w/v) Triton X-100; pH 7.4), hydrogen peroxide or manganese chloride was added, so that the final concentration of each additive was adjusted to 0.1% (w/v) or 10 mM. The thus-prepared buffers were employed as diluting buffers.

Subsequently, a predetermined amount of rSP-D was added to each diluting buffer, and incubated at 25° C. for 3 to 5 days. The liquid served as a sample liquid. As a control, the same buffer but containing no hydrogen peroxide or manganese chloride was subjected to the same treatment.

After each incubation for 3 days and 5 days, SP-D assay of the sample liquid and the control was performed in accordance with the standard operation method. Table 2 shows the results. As is clear from Table 2, the samples containing hydrogen peroxide or manganese chloride maintained antigenicity virtually at an equivalent level after treatment at 25° C. for 5 days, whereas a sample employing only a calcium ion exhibited 200 or more inactivation in antigenicity after treatment at 25° C. for 5 days.

Thus, use of a calcium ion in combination with hydrogen peroxide or manganese chloride remarkably enhanced thermal stability of SP-D. When incubation is carried out at 25° C., antigenic activity can be maintained at 90% or more after 5 days incubation.

TABLE 2

Percent activity (%) Days 3 and 5 (100% at Day 0)

| Additives | Day 3 | Day 5 |
|---|---|---|
| Control (no additive) | 85 | 78 |
| Manganese chloride | 95 | 96 |
| Hydrogen peroxide | 98 | 98 |

Example 3

Effect of Addition in the Absence of Calcium Chloride

To a buffer (10 mM HEPES, 150 mM sodium chloride, 1.0% bovine serum albumin, and 0.5% Triton X-100; pH 7.4), calcium chloride was added so that the final concentration thereof was adjusted to 10 mM; manganese chloride was added so that the final concentration thereof was adjusted to 50 mM, 10 mM, or 1 mM; or hydrogen peroxide was added so that the final concentration thereof was adjusted to 1%, 0.1%, or 0.01% (w/v); or iron (II) chloride was added so that the final concentration thereof was adjusted to 1 mM. The thus-prepared buffers were employed as diluting buffers.

Subsequently, a predetermined amount of recombinant SP-D was added to each diluting buffer and incubated at 25° C. or 37° C. for a period specified in Table 3 or 4. The liquid served as a sample liquid. As a control, the same buffer but containing no such additives was subjected to the same treatment.

SP-D assay of the control and the sample liquid was performed by means of an SP-D assay kit (product of YAMASA Corporation) in accordance with the standard operation method.

As a result, antigenic activity of SP-D can be consistently maintained in the sole presence of a manganese ion at 25° C. (Table 3), but cannot be consistently maintained at 37° C. (Table 4) in the sole presence of a manganese ion or a calcium ion.

TABLE 3

| | Percent activity (%) (vs. Day 0) | | |
|---|---|---|---|
| Additives | Day 3 | Day 5 | Day 7 |
| None | 33 | 31 | 26 |
| 50 mM Manganese chloride | 95 | 104 | 98 |
| 10 mM Manganese chloride | 93 | 105 | 97 |
| 1 mM Manganese chloride | 98 | 101 | 89 |
| 1% Hydrogen peroxide | — | 80 | 67 |
| 0.1% Hydrogen peroxide | — | <25 | <25 |
| 0.01% Hydrogen peroxide | — | <25 | <25 |
| 1 mM Iron(II) chloride | 95 | 85 | 44 |
| 10 mM Calcium chloride | 84 | 81 | 76 |

—: Not measured

TABLE 4

| | Percent activity (%) (vs. Hour 0) | | |
|---|---|---|---|
| Additives | Hour 24 | Hour 48 | Hour 120 |
| None | 25 | <25 | <25 |
| 50 mM Manganese chloride | 97 | 90 | 89 |
| 10 mM Manganese chloride | 91 | 92 | 79 |
| 1 mM Manganese chloride | 48 | 51 | <25 |
| 1% Hydrogen peroxide | <25 | <25 | <25 |
| 0.1% Hydrogen peroxide | <25 | <25 | <25 |
| 0.01% Hydrogen peroxide | <25 | <25 | <25 |
| 1 mM Iron(II) chloride | <25 | <25 | <25 |
| 10 mM Calcium chloride | 72 | 63 | 35 |

Example 4

Effect of Addition in the Presence of Calcium Chloride

To a buffer (10 mM HEPES, 150 mM sodium chloride, 10 mM calcium chloride, 1.0% bovine serum albumin, and 0.5% Triton X-100; pH 7.4); manganese chloride was added so that the final concentration thereof was adjusted to 50 mM, 10 mM, or 1 mM; iron(II) chloride was added so that the final concentration thereof was adjusted to 5 mM or 1 mM; iron (III) chloride was added so that the final concentration thereof was adjusted to 1 mM; cuprous chloride was added so that the final concentration thereof was adjusted to 1 mM; or hydrogen peroxide was added so that the final concentration thereof was adjusted to 1%, 0.1%, 0.01% (W/V). The thus-prepared buffers were employed as diluting buffers.

Subsequently, a predetermined amount of recombinant SP-D was added to each diluting buffer and incubated at 25° C. or 37° C. for a period specified in Table 5 or 6. The liquid served as a sample liquid. As a control, the same buffer containing no such additives (but containing calcium chloride) was subjected to the same treatment.

SP-D assay of the diluting control and the sample liquid was performed by means of an SP-D assay kit (product of YAMASA Corporation) in accordance with the standard operation method.

As a result, antigenic activity of SP-D can be consistently maintained in the co-presence of a calcium ion at 25° C. (Table 5) and at 37° C. (Table 6).

TABLE 5

| | | Percent activity (%) (vs. Hour 0) | | | |
|---|---|---|---|---|---|
| Additive 1 | Additive 2 | Day 3 | Day 5 | Day 7 | Day 14 |
| 10 mM Calcium chloride | None | 76 | 75 | 56 | 51 |
| | 50 mM Manganese chloride | 92 | 106 | 101 | 88 |
| | 10 mM Manganese chloride | 89 | 99 | 89 | 76 |
| | 1 mM Manganese chloride | 84 | 91 | 81 | 62 |
| | 1% Hydrogen peroxide | 84 | 95 | 88 | — |
| | 0.1% Hydrogen peroxide | 95 | 95 | 96 | 91 |
| | 0.01% Hydrogen peroxide | 83 | 90 | 103 | 68 |
| | 1 mM Iron(II) chloride | — | 102 | 86 | 88 |
| | 1 mM Iron(III) chloride | — | 104 | 93 | 99 |

—: Not measured

TABLE 6

| | | Percent activity (%) (vs. Hour 0) | | |
|---|---|---|---|---|
| Additive 1 | Additive 2 | Hour 24 | Hour 48 | Hour 120 |
| 10 mM Calcium chloride | None | 61 | 44 | 31 |
| | 50 mM Manganese chloride | 95 | 95 | 97 |
| | 10 mM Manganese chloride | 98 | 91 | 78 |
| | 1 mM Manganese chloride | 80 | 76 | 36 |
| | 1% Hydrogen peroxide | 93 | 76 | — |
| | 0.1% Hydrogen peroxide | 94 | 93 | 102 |
| | 0.01% Hydrogen peroxide | 86 | 55 | — |
| | 5 mM Hydrogen peroxide | 96 | 94 | — |
| | 1 mM Iron(II) chloride | 93 | 85 | 67 |
| | 1 mM Iron(II) chloride | 99 | 94 | 87 |
| | 1 mM Iron(III) chloride | 80 | 71 | — |
| | Cuprous chloride | | | |

—: Not measured

The invention claimed is:

1. A method for stabilizing a pulmonary surfactant protein, the method comprising causing the pulmonary surfactant protein to be present with a calcium ion in an amount of 0.001 to 100 mM and one or more oxidizing/reducing substances selected from the group consisting of hydrogen peroxide in an amount of 0.001 to 5% w/v, divalent iron in an amount of 0.001 to 1,000 mM, trivalent iron in an amount of 0.001 to 1,000 mM, divalent manganese in an amount of 0.001 to 1,000 mM, and monovalent copper in an amount of 0.001 to 1,000 mM.

2. A method as described in claim 1, wherein antigenic activity of the pulmonary surfactant protein has been stabilized.

3. A method as described in claim 1, wherein the pulmonary surfactant protein is a recombinant pulmonary surfactant protein D (rSP-D).

4. A kit for assaying a pulmonary surfactant protein present in a sample through an immunological technique employing antigen-antibody reaction, the kit containing, an aqueous standard solution comprising a pulmonary surfactant protein which has been stabilized with a calcium ion in an amount of 0.001 to 100 mM and one or more oxidizing/reducing substances selected from the group consisting of hydrogen peroxide in an amount of 0.001 to 5% w/v, divalent iron in an amount of 0.001 to 1,000 mM, trivalent iron in an amount of 0.001 to 1,000 mM, divalent manganese in an amount of 0.001 to 1,000 mM, and monovalent copper in an amount of 0.001 to 1,000 mM.

5. A kit as described in claim 4, wherein antigenic activity of the pulmonary surfactant protein has been stabilized.

6. A kit as described in claim 4, wherein the pulmonary surfactant protein is a recombinant pulmonary surfactant protein D (rSP-D).

7. The method as described in claim 1, wherein the one or more oxidizing/reducing substances is selected from the group consisting of hydrogen peroxide in an amount of 0.01 to 1% w/v, divalent iron in an amount of 0.01 to 100 mM, trivalent iron in an amount of 0.01 to 100 mM, divalent manganese in an amount of 0.01 to 100 mM, and monovalent copper in an amount of 0.01 to 100 mM.

8. The kit as described in claim 4, wherein the one or more oxidizing/reducing substances is selected from the group consisting of hydrogen peroxide in an amount of 0.01 to 1% w/v, divalent iron in an amount of 0.01 to 100 mM, trivalent iron in an amount of 0.01 to 100 mM, divalent manganese in an amount of 0.01 to 100 mM, and monovalent copper in an amount of 0.01 to 100 mM.

9. The method as described in claim 1, comprising hydrogen peroxide.

10. The method as described in claim 1, comprising divalent manganese.

11. The kit as described in claim 4, comprising hydrogen peroxide.

12. The kit as described in claim 4, comprising divalent manganese.

* * * * *